United States Patent [19]

Bayha et al.

[11] Patent Number: 4,818,363

[45] Date of Patent: Apr. 4, 1989

[54] COMBUSTION EXHAUST GAS SENSOR STRUCTURE, PARTICULARLY FOR AUTOMOTIVE ENGINE EXHAUST GASES

[75] Inventors: Kurt Bayha, Oberriexingen; Helmut Weyl, Schwieberdingen, both of Fed. Rep. of Germany

[73] Assignee: Robert Bosch GmbH, Stuttgart, Fed. Rep. of Germany

[21] Appl. No.: 461,116

[22] Filed: Jan. 26, 1983

[30] Foreign Application Priority Data

Feb. 26, 1982 [DE] Fed. Rep. of Germany ....... 3206903

[51] Int. Cl.$^4$ .............................................. G01N 27/46
[52] U.S. Cl. ...................................... 204/426; 338/34
[58] Field of Search .................. 204/15, 424, 425, 426, 204/427, 428, 429; 338/34

[56] References Cited

U.S. PATENT DOCUMENTS

| | | | |
|---|---|---|---|
| 4,019,974 | 4/1977 | Weyl et al. | 204/428 |
| 4,193,965 | 3/1980 | Cullingford et al. | 204/426 |
| 4,260,978 | 4/1981 | Yasuda et al. | 338/34 |
| 4,277,323 | 7/1981 | Muller et al. | 204/425 |
| 4,282,080 | 8/1981 | Muller et al. | 204/428 |
| 4,283,261 | 8/1981 | Maurer et al. | 204/428 |
| 4,294,679 | 10/1981 | Maurer et al. | 204/428 |
| 4,310,401 | 1/1982 | Stahl | 204/426 |
| 4,334,974 | 6/1982 | Muller et al. | 204/426 |

*Primary Examiner*—John F. Niebling
*Attorney, Agent, or Firm*—Frishauf, Holtz, Goodman & Woodward

[57] ABSTRACT

To retain a plate-like sensing element, for example made of ceramic, in position within a metallic housing without danger of breakage or loosening under conditions of vibrations or shock or wide swings of temperature and substantial temperature gradients, a metallic housing has a longitudinal opening wherein in which two sealing elements are located, for example made of aluminum oxide. The sealing elements are formed, each, with an internal pocket, for example extending conically outwardly towards their meeting surfaces, to form a chamber. The chamber is filled with a resiliently compressible powder or pulverized material, for example talcum, and separates the elements by a gap (31) extending outwardly to the walls of the metallic housing. The sensor element is passed through slits formed in the end regions of the sealing elements (26, 27) and is retained in position by the compressible powder or pulverized material. The sealing elements are retained in resiliently compressed condition, towards each other, by a spring (14, 14'), for example a washer or dish-spring, held in position and exerting direct (FIG. 1) or indirect (FIG. 4) pressure tending to compress the powdery or pulverized substance (28) surrounding the portion of the sensing element (15) therebetween, and located in said chamber. Strain-relief connections can be made to terminal portions (25) of conductive tracks (24) extending along the major surfaces of the sensing element by passing end portions of spring wire clips (FIGS. 4, 6) through suitably aligned holes or grooves in a contact guide sleeve (42).

17 Claims, 2 Drawing Sheets

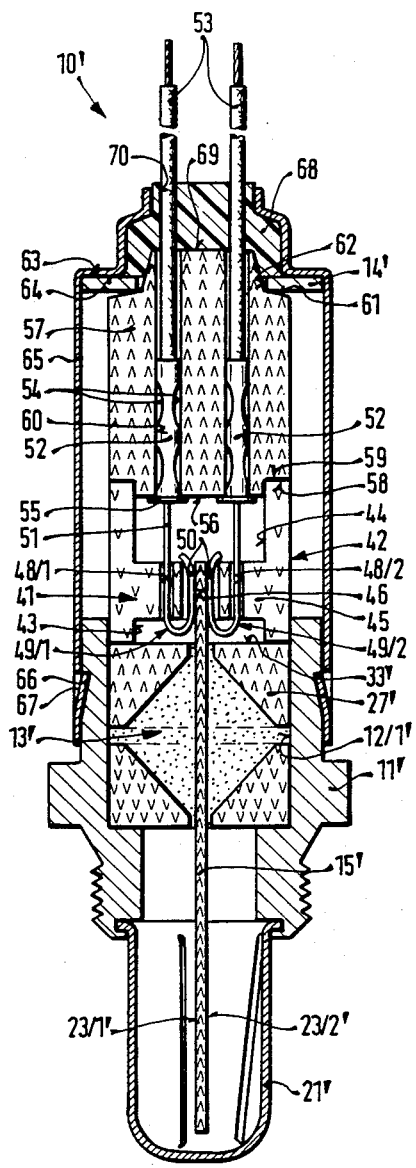
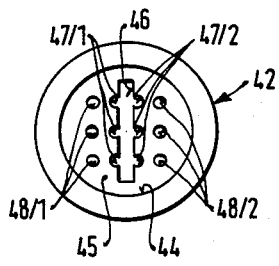
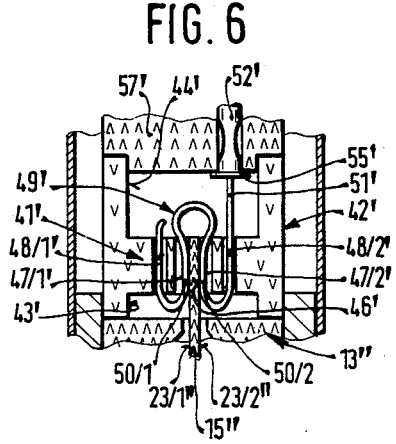

COMBUSTION EXHAUST GAS SENSOR STRUCTURE, PARTICULARLY FOR AUTOMOTIVE ENGINE EXHAUST GASES

The present invention relates to a gas sensor, and more particularly to a sensor capable of determining the oxygen content in exhaust gases resulting from a combustion process, especially combustion exhaust gases emanating from an internal combustion (IC) engine.

BACKGROUND

Various types of exhaust gas composition sensors are known; in one structure, a plate-like element is retained in a housing which is in the form of a plug capable of being screwed into a component of the exhaust system of an internal combustion (IC) engine. The actual sensing element, usually, is a structure, for example in plate form, of zirconium dioxide, which may be self-supporting or applied to a carrier substrate, for example in plate form, and which is seated in the plug. Difficulties arise in connection with holding and sealing the sensed element within the plug.

U.S. Pat. No. 4,283,261 MAURER et al, describes a gas sensor which has a sealing structure in which two matching elements, which surround the carrier, are arranged to form a pocket or chamber. The pocket or chamber is filled with a sealing material, such as glass, a cement, a hardenable putty, or the like. The glass or the cement, respectively, fills the pocket, but does not seal the region between the respective structural elements and the metal housing. It has been found that, over extended operating times, and particularly when being subjected to vibration, cement, or glass, or other rigid hardenable substances are not satisfactory for long, trouble-free operating life.

Another type of structure is disclosed in German Patent Disclosure Document No. DE-OS 26 57 541, which describes a gas sensor having a plate-like carrier positioned in a metal housing and retained therein by mean of a ceramic cement. The ceramic cement, which also forms a seal, has low resistance to vibration. Additionally, it is difficult to handle such a ceramic cement under mass production conditions. Ceramic cement is also described in U.S. Pat. No. 4,007,435, Tien; it may, for example be formed of a composition of a ceramic powder such as MgO, and sodium silicate, or a binder, such as phosphate.

U.S. Pat. No. 4,334,978, MULLER et al, assigned to the assignee of the present application, describes a sealing arrangement in which a plate-like carrier is guided through a slit formed in a metal disk secured in a metal housing. The plate-like carrier is secured behind the disk by a glass melt or by hard solder. The melt or the solder simultaneously seals the gap between the metal disk and the metal housing, as well as retaining the plate-like carrier therein. Such a seal is eminently suitable, but difficult to make economically under mass production conditions with low reject rate and high utility, and particularly when subjected to vibration or shock.

Gas sensors which have a plate-like carrier, possibly including heater elements thereon, and constructed, for example, in layer arrangement, are known in various embodiments and constructions. Examples of gas sensors with heat elements are also contained and shown in the foregoing literature references.

Electrical connection of sensor elements and heater elements are described in the foregoing references and, further, in German Patent Disclosure Document Nos. DE-OS 26 57 541 and DE-OS 25 48 019, as well as in U.S. Pat. No. 4,007,435, which show show solder connections. U.S. Pat. No. 4,157,282 describes a rivet connection for a layer-like sensor element; German Patent Disclosure Document No. DE-OS 31 50 435 discloses a plate-like carrier having depressions or through-bores formed therein through which a connecting wire can be placed, and retained by a sinterable retaining mass, for example a noble metal cermet. German Patent Disclosure Document No. DE-OS 25 26 340 shows an arrangement in which a clamping connection is referred to in the specification, although no such connection is shown in the drawing.

THE INVENTION

It is an object to provide a sensor construction in which a sensing element, for example including a plate-like carrier, can be reliably and securely retained in a metal housing structure, which can be easily contacted by a terminal unit, e.g. arranged for attachment to the sensor element, and which is easily made while being reliable in operation and resistant to damage by vibration, shock, or sharp temperature gradients, in other words, suitable for mass production manufacture and use in automotive vehicles under widely varying ambient conditions.

Briefly, a pair of electrically insulating sealing elements are located in a housing, longitudinally stacked above each other, and shaped to define, between them, a chamber or recess. The sealing elements are separated from each other by a gap. A sensor element, typically a plate-like structure, is passed through an axial opening, matching at least approximately the cross section of theplate-like element. The pocket or chamber is filled with a sealing material in the form of an electrically insulating powder, or pulverized substance, for example talcum powder, that is, a material which is resiliently compressible at all temperatures to which the sensor is expected to be exposed during quiescent as well as during operating conditions. To retain the materials resiliently compressed, a flat spring or other resiliently compressible element is provided, located in the housing and exerting compressive force against the two sealing elements which, for example, may be in the form of hollow, inwardly conical, but outwardly cylindrical plugs, fitted into the metal housing.

The structure has the advantage that the seal, and in particular the compressible, pulverized or powdery material, in combination with the elements compressed to each other, seals the entire free cross section of the longitudinal openings of the metal housing, while providing for reliable resistance against damage, even under conditions of vibration and shock. Further, the respective coefficients of expansion, under varying temperatures, can be matched to the respective elements of the sensor. The structure is simple to make so that, even under mass production conditions, the reject rate is low, and the reliability of the so made structure is high.

In accordance with a preferred feature of the invention, the insulating, compressible powder is talcum. The arrangement is particularly suitable for connection to external terminal connectors which provide for a wiping, resiliently engageable clamping contact against an exposed conductive track or electrically conductive surface on a carrier substrate. Commercial available connectors, thus, can be used, providing reliable electrical connection to sensing conductors, as well as heating conductors, if utilized by the sensor.

DRAWINGS

FIG. 4 is a longitudinal sectional view through another embodiment of a sensor, highly enlarged, in which the seal is combined with a friction clamping contact for connection to the sensor element;

FIG. 5 is a top view of a terminal guide sleeve of the terminal connection of FIG. 4; and FIG. 6 is a fragmentary view of a wiping friction contact which permits use of a single friction contact element to interconnect two major surfaces of a plate-like carrier, which both have terminal connecting surfaces located thereon.

DETAILED DESCRIPTION

Figure 1:
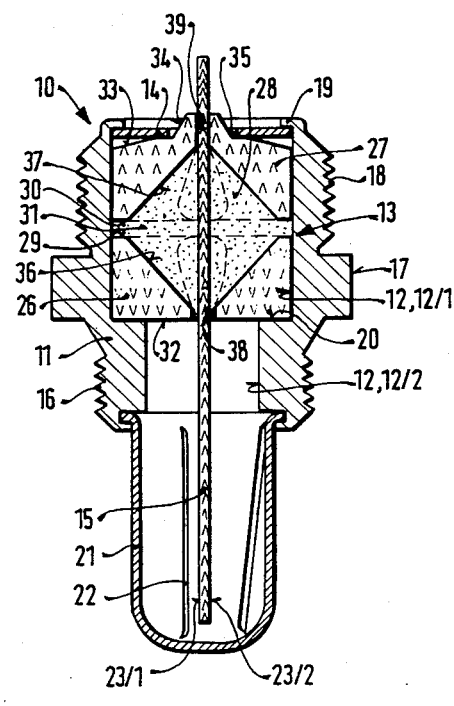
FIG. 1 is a longitudinal schematic sectional view through a sensor, to an enlarged scale.
Figure 2:
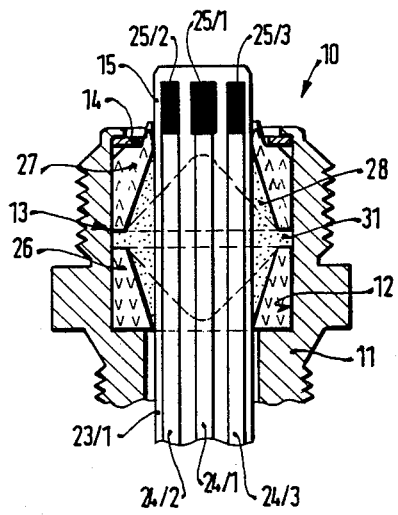
FIG. 2 is a fractional view of the sensor of FIG. 1, rotated by 90°.

The sensor 10, shown in FIGS. 1 and 2, has a metallic housing 11 which is formed with a longitudinal opening 12 therein. A multi-element seal 13 is located within the metallic housing 11. A spring, such as a spring washer, plate spring, or the like, and shown schematically at 14, presses the respective elements 26, 27 together. The elements retain a plate-like sensor carrier 15 in position. The sensor carrier 15 is held within the longitudinal opening 12 of the metallic housing. It has two end portions; at the measuring end portion, the sensor structure includes a sensor element and, if used, a layer-like heater, in accordance with any well-known structure described, for example, in the aforementioned U.S. Pat. Nos. 4,283,261 and 4,334,974.

The metal housing 11 is formed with a screw thread 16 at its outside, and, additionally, with a hex head 17, to permit installation of the sensor 10 through the wall of a duct or conduit carrying the gases to be analyzed, for example through the wall of the exhaust manifold, or part of the exhaust piping of an IC engine. Rather than using a screw thread 16 and the hex surface 17, sensors can be constructed to be fitted in openings of spaces carrying the gas to be analyzed by a push-connection, for attachment therein, for example, by separate holding screws, bonnets, or the like, and adapted for attachment through a flange formed with an opening therein.

The terminal end portion of the metal housing 11 is preferably, formed with an external screw thread 18 for connection to a holding nut or cap to hold a connector plug—not shown—in position. A guide groove to positively associate a predetermined orientation of the connector plug on the plate element 15 may be provided. The metallic housing 11 is rolled over, as seen at 19, to grip over and hold in position the spring plate or washer 14.

A shoulder 20 is formed within the metal housing 11 between the terminal end portion 12/1 and the region 12/2 facing the measuring end portion, which has a smaller inner diameter than the terminal end potion. The seal 13 is engaged by the shoulder 20 and is laterally guided within the longitudinal opening 12 in the terminal end portion 12/1.

In accordance with a preferred embodiment, the metal housing 11 has a protective sleeve or shroud 21 attached thereto, for example in form a protective tube with a closed bottom, formed with slits 22 to permit ingress and exist of the gas to be analyzed. The tube 21 surrounds the sensing carrier 15 with clearance. Protective tubes of this type usually are made of heat-resistant metal, but may also be made of ceramic.

The plate-like carrier 15 of the sensor 10 has layer-like sensor elements secured to the major surfaces 23/1 and 23/2 thereof, located at the measuring end portion of the carrier 15. At least one such sensor element is provided, connected via conductive tracks 24/1 to the terminal end portion of the carrier 15, at which contact surfaces 25/1 are formed for electrical connection to an external plug. Similarly, contacting surfaces 25/2, spaced from the surfaces 25/1, are located at the terminal end portion, and connected via conductive tracks 24/2 and 24/3 to a layer-like heater element—not shown—which is also located on the measuring end portion of the carrier 15. Examples for such sensors and heat elements are referred to above, and are known, see for example U.S. Pat. No. 4,283,261. ADditional reference may be had to German Patent Disclosure Document No. DE-OS 28 26 515 which describes sensor elements to determine the partial gas pressure and, additionally, temperature sensors, sensors to determine relative humidity, to measure the dew point, or the like, and also describes a heater. Reference may also be had to German Patent Disclosure Document No. DE-OS 31 22 861, which describes a sensor element o measure absolute air pressure.

The carrier 15 may be made of an electrically insulating material, for example aluminum oxide; it may, however, itself be an active component of a gas sensor, for example as described in the aforementioned U.S. Pat. No. 4,283,261. If the carrier 15, itself, forms an active element of the sensor structure, then, preferably, an insulating layer, for example aluminum oxide, is interposed between the conductive tracks 24/2 and 24/3 for the heater (not shown). This insulation of the heater conductive tracks eliminates influencing of the sensing signal from the sensor elements—not shown—on the carrier 15 by the heater current.

The conductive tracks 24/1, 24/2, 24/3 on the major surface 23/1, preferably, are made of platinum or a platinum metal; the conductive tracks 24/2, 24/3 for the heater element, not shown, may be made, however, also of tungsten which has a proportion of a ceramic material, for example mixed in by about 40%—by weight. The ceramic which is mixed in with the metal of the conductive tracks 24/1-24/3 preferably is the same as the material of the carrier 15.

The material of the contact surfaces 25/1-25/3 preferably is one or more platinum metal and, most suitably mixed with the same ceramic material as the substrate 15. It has been found that such contact surfaces 25/1-25/3 do not vaporize or melt at the temperatures at which sintering processes occur during manufacture of the gas sensors, while still providing excellent ceramic contact properties which extend even at high temperatures. Such excellent contact properties thus are highly suitable for high-temperature use, to which such sensors may be exposed. Contact surfaces 25/1-25/3, when to be used with a solder connection, should have a temperature persistence, without modification, up to about 500° C. Such terminal surfaces 25/1-25/3 are also excellently suitable for clamping or resilient contact engagement with a resilient contact plug.

The carrier plate 15, preferably, has a thickness of about 1 mm, and a width of about 8 mm. The conductive track 24/1 for the sensor element—not shown—has a width of about 0.8 mm; the conductive tracks 24/2 and 24/3 for the heater element—not shown—have a width, each, of 1.5 mm. The dimensions of the carrier 15, of the conductive tracks 24/1–24/3, and of the surfaces 25/1–25/3 can be matched to requirements which depend on design of the final element with which the sensor is to be used. Typically, for example, the dimensions are matched to fit into a metal housing which can readily be screwed into the wall of a portion of the combustion exhaust system of an IC engine. Sensor elements with conductive tracks 24 and terminal connecting surfaces 25 may also be applied to the second major surface 23/2 of the carrier 15.

The seal 13 is composed, essentially, of three elements: a lower element 26, an upper element 27, and electrically insulating powder or pulverized material 28.

Elements 26 and 27 are made of electrically insulating material, for example aluminum oxide. Their outer circumference is dimensioned to fit within the longitudinal opening 12/1 of the terminal portion of the housing 11. Their facing surfaces 29, 30 are so arranged that they are spaced from each other by a gap 31 which extends to the longitudinal opening 12/1 of the metallic housing 11. The end surface 32, facing the measuring end portion, of the lower element 26 is engaged by the shoulder 20 in the longitudinal opening 12 of the housing. The end surface 33 of the upper portion 27 facing the terminal end is, preferably, slightly spherical or upwardly bulged, or formed with a slightly conical or upwardly tapering surface. It is engaged, under mechanical pressure or bias, by the spring element 14. The spring element 14 is formed with an opening 35 to permit passage of a guide surface or guide portion which is formed with guide surfaces 34. The guide portion having the surface 34 also is formed with a central opening to guide the element 15 therein.

Figure 3:
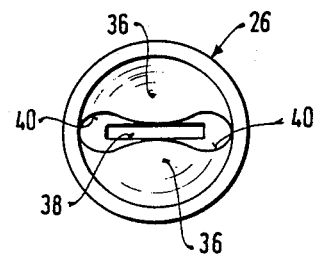
FIG. 3 is a top view of the lower sealing element of the seals of FIGS. 1 and 2.

The lower element 26 as well as the upper one 27 have interior conical surfaces 29, 30 to define, each, essentially conical pockets or chambers 36, 37, which are so placed that the diameters extend in the facing regions, whereas the diameters decrease or narrow in the direction of the end surfaces 32, 33 of the respective elements. The inner surfaces 29, 30 thus extend at an angle with respect to the carrier plate element 15. The conical surfaces terminate, respectively, in throughbores in the form of slit-like openings 38, 39 to permit passage of the carrier element 15 therethrough. The openings 38, 39 are so dimensioned that the carrier element 15 can fit snugly therein. The upper element 27 is located slidably with respect to the carrier 15 to permit slight adjustment upon changes in operating temperatures to which the sensor 10 is exposed. The end regions of the slit-like openings 38, 39 are formed with additional enlargements at their outer sides, as seen at 40 (FIGS. 3), which extend in the direction of the respective facing inner surfaces 29, 30 of the respective elements 26, 27.

The hollow space or chamber defined by the pockets 36, 37 in the elements 26, 27, as well as the gap 31 therebetween, is filled with an electrically insulating powder 28 which has the characteristics that, under the temperature to which the sensor may be exposed, it remains plastically deformable. A suitable and preferred material is talcum. The electrically insulating powder 28 is pre-shaped, by pressure, upon assembly of the sensor into a shape permitting the double-cone, pre-pressed talcum plug—formed with a longitudinal opening—to be threaded on the carrier plate 15. The electrically insulating powder 28 contacts the interior of the metal housing 11 in the region of the gap 31 between the two elements 26, 27, and thus provides for sealing also of the elements 26, 27 against the lateral side walls of the metal housing 11. Due to differential expansion, under different temperature conditions of operation of the sensor, of the materials of the metal housing 11, the elements 26, 27, the carrier 15 and the electrically insulating powder, changes in dimensional relationships may occur, which can readily be compensated by change in the position of the spring element 14. The seal 13 provides for a reliable sealing of the element 15 within the ceramic elements 26, 27, and of the ceramic elements 26, 27 within the metal housing; additionally, the seal 13 is resistant to damage or loosening under conditions of vibrations, shocks and jolts, and thus has high reliability in operation, even when made under mass-production conditions.

Embodiment of FIG. 4: The sensor 10' has a metallic housing 11' formed with a longitudinal opening therein. In the portion 12/1' of the longitudinal opening, a seal 13' in accordance with the invention is retained. The difference between the embodiment of FIG. 4 and FIG. 1 is, essentially, in the shape of the metal housing 11, which does not have an outer thread 18 for a terminal plug, and does not have the rolled-over edge 19. The general construction, however, is essentially identical to the embodiment of FIG. 1, except that the spring element 14 is replaced by a spring element 14' which is located at a different position. The sensor carrier 15', located in the region of the sensor 10', the contacting surfaces, and all other constructional features relating to the sensor, heater elements, conductive tracks, and the like, as well as the protective sleeve or tube 21', are identical to the sensor 10 shown in FIG. 1.

In accordance with the embodiment of FIG. 4, the sensor 10', with the seal 13' in accordance with the invention, is additionally provided with a pressure contact arrangement 41 which is strain-relieved with respect to the contacting terminal strips on the carrier 15'. The preferably flat facing end surface 33' of the upper sealing element 23' has an electrically insulating contact guide sleeve 42 located thereon which is retained within the metal housing 11' at its outer circumference. A preferred material for the sleeve 42 is aluminum oxide. FIG. 5 illustrates the arrangement of the sleeve 42 which, at the side facing the measuring end portion of the sensor, has a coaxial recess 43. At the side facing the terminal, a coaxial recess 44 is formed therein. An intermediate element 45 is located between the recesses 43, 44. A slit 46, with lateral grooves 47/1, 47/2, is formed in the intermediate element 45 of the sleeve 42, extending longitudinally with respect to the sensor 10'. Through-bores 48/1, 48/2 are, additionally, formed in the intermediate region 45, laterally of the grooves 47/1, 47/2—see FIG. 5. Friction pressure contact elements 49/1, 49/2, which are shaped as bent-backwardly resilient elements are threaded through the respective holes 48/1, 48/2, with a short, free-end terminal of the clamping friction contact 50 being received in one of the grooves 47, to engage a contact surface on the carrier 15'. The contact surfaces have been omitted from the carrier 15' in FIGS. 4 and 6, for ease of illustration, but can be constructed similarly to the contact surfaces 25 of FIG. 2.

In a preferred form of the invention, see FIG. 4, on respective engaging contact element 49/1 is located immediately opposite another contact element 49/2, so that the respective contact elements engage at opposite major surface 23/1', 23/2' of the carrier 15', to securely clamp the carrier between the resilient hook or bent-over elements of the connecting wires for reliable resilient mechanical as well as electrical contact. The extending leg 51 of the contact element then is threaded through the through-bores 48. This arrangement eliminates application of bending stresses on the carrier 15', clamped in the seal 13'. If only one of the major surfaces 23/1', or 23/2', of the carrier 15' has contact surfaces thereon, a single clamping element 49 would suffice; it is, then, desirable, however, to so arrange the slit 46 in the contact guide sleeve 42 that the region of the carrier 15' which is not contacted by a resilient element can bear against a surface within the carrier sleeve 42 defining the slit 46, to prevent application of bending stresses on the carrier 15'.

The legs 51 of the clamping terminals 49, which are positioned within the recess 44, are connected to a metallic connecting sleeve 52 which, in turn, is connected to a blank terminal end of an insulated connecting cable 53. The respective legs 51 of the clamping terminal 49 and the metallic end portion of the cable 53 are connected in the sleeve 52 by a punch, crimp, or other suitable electrical connection. Each sleeve 52 is formed with a flange 55 which is located in the recess 44 of the connecting guide sleeve 42. The flange 55 of the sleeve 52 engages a surface 56 of an insulating element 57. The insulating element 57, for example in form of a plug, is located coaxially to the longitudinal opening of the sensor 10'. The plug 57 is centered to the metallic housing 11', and is formed with a shoulder 58 which engages with the end surface 59 of a projecting end portion of the body 42. The insulating plug 57, preferably, is made of aluminum oxide, or similar suitable material, and retains, in longitudinal bores 60, the connecting sleeves 52 and portions of the insulating connecting cable 53. The terminal end portion of the insulating body 57 is formed with a shoulder 61 which, preferably, slightly decreases in length at the outer edges to receive the spring element 14', formed with a hole 62, and surrounding the insulating plug 57. The terminal end portion of the spring element 14' engaged at its outer edge a shoulder 64 of a metal sleeve 65 which coaxially surrounds the sensor 10' up to the terminal end region of the metal housing 11'. Punched-in flaps 66, engaging in punch marks or notches 67 of the metal housing, secure the metal sleeve 65 on the metal housing 11', and also insure that the spring element 14' will be mechanically stressed.

The terminal end portion of the metal sleeve 65 is cup-shaped and does not have a full bottom region; it includes an elastic, heat-resistant sealing plug 68, for example made of a rubbery or plastic material, e.g. silicone rubber, which is fitted on the spring element 14' and on the terminal end surface 69 of the electrically insulating body 57, and seals the insulating body 57, as well as through-bores 70 for the cable 53, to provide a moisture-proof, yet resilient sealing arrangement.

The cables 53, due to the flange 55, are retained within the sensor, and strain-relieved by engagement of the flange 55 against the surface 56 of the plug 57.

FIG. 6 illustrates an embodiment of a friction-clamping connection 41', which is particularly suitable if the carrier 15" is formed on its major surfaces 23/1" and 23/2" with oppositely located contact surfaces which are connected to respective layer-like sensors or heat elements, and which are also to be connected together. The heater and sensor element structures, themselves, are not shown, and may be in accordance with any well-known arrangement.

The contact guide sleeve 42' has a slit 46' and a first through-bore 48/1', a second through-bore 48/2', and grooves 47/1', 47/2', similar to the sleeve 42 of FIG. 4. The clamping contact element 49', however, is changed in that the leg 51' which extends from the clamping sleeve 52' beyond the flange 55' thereof, is fitted through the second through-bore 48/2', then threaded upwardly through the groove 47/2', and engaging the contact surface of the major surface 23/2' as a terminal contact 50/2. It then extends into the recess 44' of the contact guide sleeve 42', and is bent over itself, backwardly, again in the first original direction to fit into the groove 47/1' of the slit 46' and forms a clamping terminal 50/1 on the second major surface 23/1' of the sensor element 15'. The free end of the clamping element 50/1 then is bent over itself, backwardly, to fit into the groove 48/1' of the contact guide sleeve 42'. The flange 55', thus, forms a strain relief fitting against the insulating body 57', which retains the connecting sleeve 52'.

The friction clamping connection 41', thus, requires only a single terminal element 49' for oppositely located contact zones, and, further, is so arranged that no bending or torsion stresses will be applied to the carrier 15' held at the end portion of the seal 13'.

Various changes and modifications may be made, and features described in connecting with any one of the embodiments may be used with any of the others, within the scope of the inventive concept.

We claim:

1. Gas sensor structure to sense the composition of combustion exhaust gases, particularly exhaust gases from an internal combustion engine, having a metallic housing (11) having a sensing end portion and a terminal end portion, said housing being formed with an elongated opening therethrough;

an elongated plate-like sensing element having a sensing end region and a terminal end region, and including a carrier element in the form of an elongated plate (15);

electrode connection means (24) located on the surface of the sensing element and extending towards the sensing end region;

retaining means (26, 27) securing the sensing element in the metallic housing at an intermediate region of the sensing element, including two electrically insulating retaining elements (26,27) shaped to define a chamber therebetween, in which the intermediate region of the sensing element is received in a manner subdividing said chamber into a pair of opposite subchambers communicating with each other around the lateral edges of said elongated plate;

abutment means (20) for supporting one of said retaining elements in the housing;

wherein the electrically insulating retaining elements (26,27) are positioned in the metallic housing in longitudinally aligned, stacked position, and separated from each other by a gap (31), both retaining elements, inwardly of the metallic housing, being formed with a through-bore in form of a terminal slit (38,39) through which said plate-like sensing element passes, and with a chamber-forming recess (36,37), the recesses in said retaining elements jointly defining said chamber, said recess of each said retaining element expanding from said terminal slit to an enlarged recess region adjacent the gap (31) by way of diverging retaining element surfaces (29,30) which are oblique with respect to the plane of the plate (15);

and wherein sealing material (28) is located in said chamber as well as in said gap (31), extending, in said gap, radially outwardly to engage the inner walls of the metallic housing, the surfaces (29,30) of said retaining elements bounding said recesses (36,37) thereof defining said chamber, and surface portions of said plate (15) located within said chamber, thereby completely filling the chamber and the gap, and comprises an electrically insulating powder or pulverized material which is resiliently compressible at all temperatures to which the sensor is exposed, during quiescent as well as operating conditions;

and wherein resilient compression means (14, 14') are provided, located in the housing and exerting a compression force against said retaining elements (26,27) tending to resiliently compress the electrically insulating powder or pulverized material in the chamber and in said gap between the retaining elements and exerting compressive force against the surface portions of said plate located within said chamber, said sensing element (15) passing through and being retained in position by said powder or pulverized material exerting compressive force against said surface portions of said plate thereof.

2. Sensor according to claim 1, wherein the electrically insulating compressible powder or pulverized material (28) comprises talcum.

3. Sensor according to claim 2, wherein the recesses (36, 37) formed in said retaining elements (26, 27) are essentially conical, with the widest diameter in the region of the gap (31).

4. Sensor according to claim 3, wherein the recesses in said retaining elements are additionally formed with pockets (40) in the region of the slits (38,39), which pockets extend or become enlarged in the direction towards said gap (31).

5. Sensor according to claim 1, wherein the abutment means comprise a counter surface formed in the housing and a support surface (19) is provided on ths housing holding the resilient compressible means (14, 14') to provide application of compressive force against said compressible powder or pulverized material.

6. Sensor according to claim 1, wherein
contact surfaces (25/1-25/3) are formed at the terminal regions of the plate-like structure electrically connected to said connection means (24); and
said contact surfaces are positioned on said sensing element in a zone beyond the sealing element (27) remote from the sensing region.

7. Sensor according to claim 6, further including (FIGS. 4-6) an electrically insulating contact guide sleeve (42) longitudinally stacked above said retaining element (27) remote from the sensing region, said contact guide sleeve (42) being formed with a longitudinal slit (46) receiving the sensing element (15') in the region of its contacting surfaces (25);

and frictional, resiliently clampable contact elements (49/1, 49/2) are provided, secured in said contact guide sleeve and resiliently engageable with the contact surfaces on the sensing element.

8. Sensor according to claim 7, further including connecting cables (53) electrically and mechanically connected to said resiliently clampable contact elements;

a cable guide sleeve (57) stacked on said contact guide sleeve (42) retaining and guiding said connecting cables (53), said cable guide sleeve (57) being compressibly resiliently retained in contact with the contact guide sleeve by said resilient compression means (14').

9. Sensor according to claim 8, further including a metal protective sleeve 965) surrounding said cable guide sleeve and mechanically connected to and retained on said metal housing (11');

the resilient compression means (14') being a spring element retained within the metal protective sleeve and engaging a shoulder (64) thereon, coaxial with respect to the metal housing (11), to compress said retaining elements (26', 27') towards each other, and said said resiliently compressible powder or pulverized material, by indirect pressure via said contact guide sleeve (42).

10. Sensor according to claim 7, wherein said contact guide sleeve (42) is formed with through-bores (48/1, 48/2) to receive portions (51) of said contact element (49/1, 49/2) and retain said elements within the contact guide sleeve;

and wherein said contact elements are formed with resiliently deflectable reverse-bends positioned adjacent the slit (46) for engagement with contact surfaces (25) on the sensor element (15');

and strain-relieved connection means (52, 55) are provided for connecting the portions of the contact elements to externally accessible connecting cables (53).

11. Sensor according to claim 10, wherein the slit 946) is formed with lateral grooves (47/1, 47/2) to guide the reverse-bends of said contact elements and locate them adjacent the contact regions (25) of the sensor element (15).

12. Sensor according to claim 11, wherein the strain-relieved connection means comprises a compression terminal (52) formed with a flange (55).

13. Sensor according to claim 8, further including strain-relief connection means connecting the contact elements (49/1, 49/2) to the connecting cables including
a terminal sleeve (52) located in said cable guide element 957) and formed with an outer flange (55) bearing against an end surface of the cable guide sleeve (57) to form a strain relief and prevent transfer of strain on the connection cables (53) to said resiliently clampable contact elements (49/1, 49/2).

14. Sensor according to claim 10, wherein the contact elements (49') include a double-bent end portion arranged to engage two major surfaces (23/1", 23/2") of the sensor element (15") at aligned, oppositely positioned regions, for connection of terminal surfaces (25) located on said oppositely located major surfaces, and to provide uniformly distributed compressible forces against the sensor element, the reversely bent portions being secured in the contact guide sleeve to provide uniform resilient compressive force against the two major surfaces of the sensor element, and thus eliminate application of unilateral bending stresses thereon by said resiliently clampable contact elements.

15. Sensor according to claim 5, wherein the electrically insulating compressible powder or pulverized material (28) comprises talcum.

16. Sensor according to claim 7, wherein the electrically insulating compressible powder or pulverized material 928) comprises talcum.

17. Sensor according to claim 1, wherein the recesses (36, 37) formed in said retaining elements (26, 27) are essentially conical, with the widest diameter in the region of the gap (31).

* * * * *